(12) United States Patent
Shalaby

(10) Patent No.: US 8,083,805 B2
(45) Date of Patent: *Dec. 27, 2011

(54) ABSORBABLE ENDO-UROLOGICAL DEVICES AND APPLICATIONS THEREFOR

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1149 days.

This patent is subject to a terminal disclaimer.

(21) Appl. No.: 11/204,822

(22) Filed: Aug. 16, 2005

(65) Prior Publication Data

US 2007/0042018 A1    Feb. 22, 2007

(51) Int. Cl.
*A61F 2/04*   (2006.01)
*A61M 5/00*   (2006.01)
*A61F 2/06*   (2006.01)

(52) U.S. Cl. .......... 623/23.66; 623/1.32; 623/1.33; 623/1.38; 623/1.49; 623/1.5; 623/1.54; 623/23.7; 604/8

(58) Field of Classification Search ............ 623/23.7, 623/23.66, 1.32–1.33, 23.64, 23.65, 23.67–23.69, 623/1.38, 1.49–1.54; 604/8, 9
See application file for complete search history.

(56) References Cited

U.S. PATENT DOCUMENTS

| | | | |
|---|---|---|---|
| 5,629,077 A | | 5/1997 | Turnlund et al. |
| 5,633,343 A * | | 5/1997 | Bezwada et al. ............ 528/361 |
| 5,674,241 A * | | 10/1997 | Bley et al. .................. 623/1.2 |
| 5,674,286 A * | | 10/1997 | D'Alessio et al. ......... 424/423 |
| 5,792,400 A * | | 8/1998 | Talja et al. ................. 264/103 |
| 6,017,362 A * | | 1/2000 | Lau ............................. 623/1.2 |
| 6,211,249 B1 * | | 4/2001 | Cohn et al. ................ 514/772.1 |
| 6,245,103 B1 * | | 6/2001 | Stinson ...................... 623/1.22 |
| 6,338,739 B1 * | | 1/2002 | Datta et al. ................ 623/1.15 |
| 6,342,065 B1 * | | 1/2002 | Shalaby ...................... 606/230 |
| 6,462,169 B1 | | 10/2002 | Shalaby |
| 6,517,575 B1 * | | 2/2003 | Yang et al. ................. 623/1.44 |
| 6,524,345 B1 | | 2/2003 | Valimaa et al. |
| 6,585,773 B1 | | 7/2003 | Xie |
| 6,605,294 B2 * | | 8/2003 | Sawhney .................... 424/426 |
| 6,685,734 B1 | | 2/2004 | Valimaa et al. |
| 6,699,940 B2 * | | 3/2004 | Shalaby ...................... 525/308 |
| 6,733,536 B1 | | 5/2004 | Gellman |
| 6,747,121 B2 * | | 6/2004 | Gogolewski ............... 528/354 |
| 7,465,489 B2 | | 12/2008 | Shalaby et al. |
| 7,794,495 B2 * | | 9/2010 | Gale et al. .................. 623/1.49 |
| 7,803,182 B2 * | | 9/2010 | Dave et al. ................. 623/1.38 |
| 2001/0021873 A1 | | 9/2001 | Stinson |
| 2002/0031601 A1 | | 3/2002 | Darouiche et al. |
| 2002/0155159 A1 | | 10/2002 | Shalaby |
| 2002/0161168 A1 * | | 10/2002 | Shalaby et al. ............ 528/310 |
| 2003/0009213 A1 * | | 1/2003 | Yang ........................... 623/1.13 |
| 2003/0069629 A1 | | 4/2003 | Jadhav et al. |
| 2003/0120029 A1 * | | 6/2003 | Shalaby et al. ............ 528/310 |
| 2003/0153983 A1 * | | 8/2003 | Miller et al. ............... 623/23.7 |
| 2003/0162940 A1 | | 8/2003 | Shalaby |
| 2003/0190406 A1 * | | 10/2003 | Hossainy et al. .......... 427/2.25 |
| 2003/0209835 A1 | | 11/2003 | Chun et al. |
| 2004/0028655 A1 * | | 2/2004 | Nelson et al. .............. 424/93.2 |

(Continued)

*Primary Examiner* — David Isabella
*Assistant Examiner* — Andrew Iwamaye
(74) *Attorney, Agent, or Firm* — McCormick, Paulding & Huber LLP

(57) ABSTRACT

This invention deals with an absorbable/disintegratable endo-urological stent and applicators for introduction into biological conduits, including such as urethras and ureters, with said stent comprising a fiber-reinforced, multicomponent tube made of polyesters having a range of physicochemical properties.

16 Claims, 2 Drawing Sheets

U.S. PATENT DOCUMENTS

| | | | |
|---|---|---|---|
| 2004/0044397 A1* | 3/2004 | Stinson | 623/1.15 |
| 2004/0120981 A1* | 6/2004 | Nathan | 424/426 |
| 2004/0133237 A1* | 7/2004 | Shalaby | 606/230 |
| 2004/0138644 A1 | 7/2004 | DiCarlo et al. | |
| 2004/0138738 A1 | 7/2004 | Stinson | |
| 2004/0249441 A1 | 12/2004 | Miller et al. | |
| 2004/0249450 A1* | 12/2004 | Ishii | 623/1.44 |
| 2005/0149175 A1* | 7/2005 | Hunter et al. | 623/1.42 |
| 2005/0163821 A1* | 7/2005 | Sung et al. | 424/426 |
| 2006/0018948 A1* | 1/2006 | Guire et al. | 424/426 |
| 2006/0025848 A1* | 2/2006 | Weber et al. | 623/1.15 |
| 2006/0178739 A1* | 8/2006 | Shalaby et al. | 623/1.49 |
| 2007/0038290 A1* | 2/2007 | Huang et al. | 623/1.16 |

* cited by examiner

ABSORBABLE ENDO-UROLOGICAL DEVICES AND APPLICATIONS THEREFOR

FIELD OF THE INVENTION

This invention relates to absorbable/disintegratable corrective devices and applicators therefore that are useful in maintaining optimum patency of conduits in the urinogenital tract as exemplified by endo-urological stents to maintain optimum ureteral or urethral patency for a predetermined period of time. At the conclusion of this period, the device is expected to have practically no physical presence that may interfere with pertinent biological functions.

BACKGROUND OF THE INVENTION

As a result of endo-urological advances, biomaterials, and particularly absorbable or transient ones, are increasingly being used in the urinary tract. A typical illustration of such uses is provided in U.S. Pat. No. 6,733,536 dealing with a urethral stent device. In this disclosure, a stent for treatment of a body lumen through which a flow is effected on either side of a sphincter was described, the stent comprising one or more windings and having an inner core substantially covered by an outer core and including a first segment, a second segment, and a connecting member disposed between the segments. When the stent is positioned within a patient's urinary system, the first segment and second segments are located on either side of the external sphincter to inhibit migration of the stent while not interfering with the normal functioning of the sphincter. The outer coating comprises an absorbable material that provides temporary structural support to the stent. After absorption of substantially all the outer coating of the stent, the remaining relatively compliant inner core facilitates easy removal by the patient by pulling a portion of the stent that extends outside the patient's body for this purpose.

In a review by Beiko and coworkers [*J. Urology*, 171, 2438 (2004)], it was noted that (1) the ideal substance for urinary tract biomaterial should incorporate certain features, such as biological inertness, chemical stability in urine, resistance to infection and encrustation, excellent long-term urinary flow, stability following placement, and no significant discomfort to the patient; and (2) urethral stents made of self-reinforced 80/20 l-lactide/glycolide copolymer were inserted in situ via cystoscopy into rabbit prostatic urethra and was found to be soft and almost completely degraded at three months—the material did not encroach into the urethral wall and there was no encrustation.

U.S. Pat. No. 6,585,773 describes an insertable stent for joining together and facilitating healing of adjacent tissues as in the case of sutureless end-to-end urethral and heterograft anastomosis. U.S. Pat. No. 6,685,734 describes a device for inserting a stent in a body cavity, particularly useful for inserting a stent into a human male urethra to treat prostatic hyperplasia, whereby such device has an elongated member for removably receiving a stent and means capable of protruding from the member to either locate an obstruction, such as the sphincter muscle, in the body cavity or to prevent the stent from sliding off of the member, or both. And U.S. Pat. No. 6,524,345 describes a suitable composition for constructing the stent described in U.S. Pat. No. 6,685,734. That composition comprises a biodegradable polymer interdispersed with ceramic particulates that are visible by radioscopy. However, none of the prior art described a combination of absorbable endo-urological stent and non-absorbable applicator combination that permit facile insertion and secured location/maintenance of the stent at the intended site, wherein said insertion is associated with predictable change in stent configuration and dimensions to insure secure immobilization, prevent migration, maintain uninterrupted functionality over a predetermined period of time, and eventual safe, regulated disintegration and absorption. This provided an incentive to pursue the present invention.

SUMMARY OF THE INVENTION

This invention deals generally with absorbable/disintegratable corrective devices and applicators therefore that are useful in maintaining optimum patency of conduits in the urinogenital tract as exemplified by endo-urological stents to maintain optimum ureteral or urethral patency for a predetermined period of time. At the conclusion of this period, the device is expected to have practically no physical presence that may interfere with pertinent biological functions.

An important aspect of this invention deals with an absorbable/disintegratable endo-urological stent comprising a fiber-reinforced, multicomponent polymeric slit tube wherein the opposing edges of said slit can be compressively overlapped under stress within a rigid, tubular applicator to yield a partially rolled configuration having an outside diameter that is at least 2 percent less than that of the parent unslit tube and whenever the stress is released at the site of a renal conduit. Upon discharging from the rigid tubular applicator the slit edges spring back almost instantly to acquire a nominal diameter that is at least 2 percent larger than that of the biological conduit wherein the reinforcing fibers of the multicomponent slit tube comprising a solid microdispersion made of (a) a copolylactide dispersed phase having at least 65 percent of its chain repeat units derived from lactide and a copolyglycolide as the continuous phase having at least 65 percent of its chain repeat units derived from glycolide; (b) a copolycarprolactone dispersed phase having at least 90 percent of its chain repeat units derived from $\epsilon$-caprolactone and a copolyglycolide as a continuous phase having at least 65 percent of its chain repeat units derived from glycolide; or (c) a copolycarprolactone dispersed phase having at least 90 percent of its chain repeat units derived from $\epsilon$-caprolactone and copolylactide as a continuous phase having at least 65 percent of its chain repeat units derived from lactide.

A specific aspect of this invention deals with an absorbable/disintegratable endo-urological stent comprising a fiber-reinforced, multicomponent polymeric slit tube wherein the opposing edges of said slit can be compressively overlapped under stress within a rigid, tubular applicator to yield a partially rolled configuration having an outside diameter that is at least 2 percent less than that of the parent unslit tube and whenever the stress is released at the site of a renal conduit upon discharging from the rigid tubular applicator the slit edges spring back almost instantly to acquire a nominal diameter that is at least 2 percent larger than that of the biological conduit, wherein the reinforcing fibers of the multicomponent slit tube comprising a block copolymer of solid polyethylene glycol and a copolyester derived from one or more monomer selected from the group represented by l-lactide, glycolide, caprolactone, trimethylene carbonate and p-dioxanone. It is also preferred that such reinforcing fibers comprise highly oriented crystalline monofilaments having a tensile modulus that exceed 500 kpsi.

Another aspect of this invention deals with an absorbable/disintegratable endo-urological stent comprising a fiber-reinforced, multicomponent polymeric slit tube wherein the opposing edges of said slit can be compressively overlapped under stress within a rigid, tubular applicator to yield a partially rolled configuration having an outside diameter that is at least 2 percent less than that of the parent unslit tube and whenever the stress is released at the site of a renal conduit upon discharging from the rigid tubular applicator the slit edges spring back instantly to acquire a nominal diameter that is at least 2 percent larger than that of the biological conduit, wherein the slit fiber-reinforced multicomponent polymeric tube comprises a highly drawn monofilament as a reinforcing component to a crosslinked, compliant matrix. It is also preferred that the crosslinked matrix is based on a triaxial polyester with reactive itaconate end-groups and a chain derived from one or more monomer selected from the group represented by ϵ-caprolactone, trimethylene carbonate, glycolide, l-lactide, dl-lactide, and p-dioxanone.

Another aspect of this invention addresses a method for producing the absorbable/disintegratable slit-tube type endo-urological stent described above entailing the steps of (a) winding the highly drawn monofilament as described above onto a highly polished or Teflon-coated stainless steel rod with the desired outside diameter to yield the nominal diameter of the final device; (b) dip-coating the wound monofilament with the polyaxial polymer, with or without dilution with a solvent, of claim 8 that contains a moderate-temperature free-radical initiator, such as azo-bis-butyronitrile; (c) incremental heating of the assembled composite to achieve matrix curing; and (d) slitting the tube at one side longitudinally using laser or ultrasonic means.

A clinically relevant aspect of this invention deals with the slit-tube type endo-urological stent as described above and method for applying the stent that entails the steps of (a) coating the external wall of the slit tube with an absorbable nonionic surfactant; (b) compress-folding, partially, the coated slit tube to yield a partially rolled configuration having a diameter that is at least 10 percent less than that of the original unslit tube; (c) inserting the partially rolled device into a relatively rigid tubular applicator made of polished stainless steel or high modulus polymer; (d) applying a non-ionic absorbable surfactant on the outer surface of the applicator and inserting it into a hermetically sealable foil pack, under dry nitrogen, that comprises a dry cellulose applicator holder and a solid plunger (for discharging the device at the biological site); (e) sterilizing the slit tube in the applicator according to an accepted protocol; and (f) introducing the hollow component of the applicator using a plunger with a controlled motion arm that is barely touching the slit tube during insertion and able to push the slit tube out of the applicator following the disengagement of the motion arm from a special bay at the applicator wall.

Another major aspect of this invention deals with an absorbable/disintegratable endo-urological composite tubular stent comprising a highly elastomeric, water-swellable matrix reinforced with a rigid spring wherein (a) said spring comprising a multicomponent, high modulus, absorbable polymer; (b) the spring exhibiting a nominal diameter that is at least 2 percent less than that of the urological conduit sought for its application; (c) the elastomeric matrix component of the stent is made of a crosslinked absorbable copolymer that is asymmetrically placed to have more than 60 percent of its mass covering the outer surface of the spring; and (d) the elastomeric matrix component is capable of swelling in the biological environment to result in at least a 30 percent increase in thickness and a highly compliant surface intimately adhering to the lumen of the biological conduit, wherein the reinforcing fibers of the composite tubular stent comprising a solid microdispersion made of (a) a copolylactide dispersed phase having at least 65 percent of its chain repeat units derived from lactide and a copolyglycolide as the continuous phase having at least 65 percent of its chain repeat units derived from glycolide; (b) a copolycarprolactone dispersed phase having at least 90 percent of its chain repeat units derived from ϵ-caprolactone and a copolyglycolide as a continuous phase having at least 65 percent of its chain repeat units derived from glycolide; or (c) copolycarprolactone dispersed phase having at least 90 percent of its chain repeat units derived from ϵ-caprolactone and copolylactide as a continuous phase having at least 65 percent of its chain repeat units derived from lactide.

A specific aspect of this invention deals with an absorbable/disintegratable endo-urological composite tubular stent comprising a highly elastomeric, water-swellable matrix reinforced with a rigid spring wherein (a) said spring comprising a multicomponent, high modulus, absorbable polymer; (b) the spring exhibiting a nominal diameter that is at least 2 percent less than that of the urological conduit sought for its application; (c) the elastomeric matrix component of the stent is made of a crosslinked absorbable copolymer that is asymmetrically placed to provide more than 60 percent of its mass surrounding the outer surface of the spring; and (d) the elastomeric matrix component is capable of swelling in the biological environment to result in at least a 30 percent increase in thickness and a highly compliant surface intimately adhering to the lumen of the biological conduit, wherein the reinforcing spring of the multicomponent composite tube comprising a block copolymer of a solid polyethylene glycol and a copolyester derived from one or more monomer selected from the group represented by l-lactide, glycolide, caprolactone, trimethylene carbonate and p-dioxanone. It is also preferred that such reinforcing spring comprise highly oriented crystalline monofilaments having a tensile modulus that exceed 500 kpsi.

Another aspect of this invention deals with an absorbable/disintegratable endo-urological composite tubular stent comprising a highly elastomeric, water-swellable matrix reinforced with a rigid spring wherein (a) said spring comprising a multicomponent, high modulus, absorbable polymer; (b) the spring exhibiting a nominal diameter that is at least 2 percent less than that of the urological conduit sought for its application; (c) the elastomeric matrix component of the stent is made of a crosslinked absorbable copolymer that is asymmetrically placed to provide more than 60 percent of its mass surrounding the outer surface of the spring; and (d) the elastomeric matrix component is capable of swelling in the biological environment to result in at least a 30 percent increase in thickness and a highly compliant surface intimately adhering to the lumen of the biological conduit, wherein the spring reinforced multicomponent polymeric tube comprises a highly drawn monofilament as the reinforcing component to a crosslinked, compliant matrix. It is also preferred that the crosslinked matrix is based on a triaxial polyester with reactive itaconate end-groups and a chain derived from one or more monomer selected from the group represented by ϵ-caprolactone, trimethylene carbonate, glycolide, l-lactide, dl-lactide, and p-dioxanone.

Another aspect of this invention addresses a method for producing the absorbable/disintegratable endo-urological stent as described above entailing the steps of (a) winding the highly drawn monofilament onto a highly polished or Teflon®-coated stainless steel rod with the desired outside diameter to yield the nominal internal diameter of the final device; (b) dip-coating the wound monofilament with the polyaxial polymer described earlier, with or without dilution with a solvent that contains a moderate-temperature free-radical initiator, such as azo-bis-butyronitrile; (c) adjust the coating thickness to provide required outside diameter of the device after curing/drying; and (d) incremental heating of the assembled composite to achieve matrix curing.

A clinically relevant aspect of this invention deals with the composite tubular-type endo-urological stent described above and method for assembling the construct for future use, which entails (a) coating the external wall with a nonionic, lubricous copolyester; (b) assembling in an applicator similar to those used for endovascular stent placement with an extensible balloon; and (c) sterilizing the assembled device in a hermetically sealed foil pack.

BRIEF DECRIPTION OF THE FIGURES OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

DETAILED DESCRIPTION OF PREFERRED EMBODIMENTS

The widespread use of biomaterials in the urinogenital tract, such as urinary catheters and ureteral stents, will undoubtedly continue into the future. This and an increasing percentage of the geriatric population and associated complications due to compromised conduit functionality, directed the attention of many investigators to the use of polymeric endo-urological stents, and particularly the absorbable types, to obviate the need for removal following the conclusion of their corrective function. Most, if not all, stents of the prior art have either tubular of spiral geometries that lack radial and/or axial elasticity/resilience leading to limited biomechanical compatibility and resistance to migration during end use and secured residence at the application site. This is particularly important in the case of ureteral stents, which constantly experience pulsatile forces. And the stent design subject of the present invention does, in-part, address this issue. In effect, the slit tubular design of the radially resilient elastic construct, subject of this invention, permits synchronized changes in the device nominal diameter with those of the ureteral wall under the prevailing pulsatile forces. From a design perspective, this invention also deals with a stent construct comprising (1) a highly oriented, monofilament-based scaffold or reinforcing filler that is radially strong and resilient to secure its mechanical stability at the application site; and (2) a crosslinked, highly compliant matrix to prevent premature extrusion of partially degraded fragments of the scaffold. A preferred feature of the present invention deals with having at least one component that swells readily in the biological environment to maximize the biomechanical compatibility of the device with the mucosal lining of the urinogenital conduits and more specifically those of the urological tract. And the slit tube design with rigid ribs and soft connecting matrix also allows the use of the device in different lengths and, more importantly, at lengths exceeding 10 cm, a requirement that cannot be fulfilled by any of the stents disclosed in the prior art. On the other hand, the tubular composite stent, as discussed later, features a rigid scaffold in a highly flexible matrix to insure radial mechanical stability and axial stretchability.

Figure 1A:
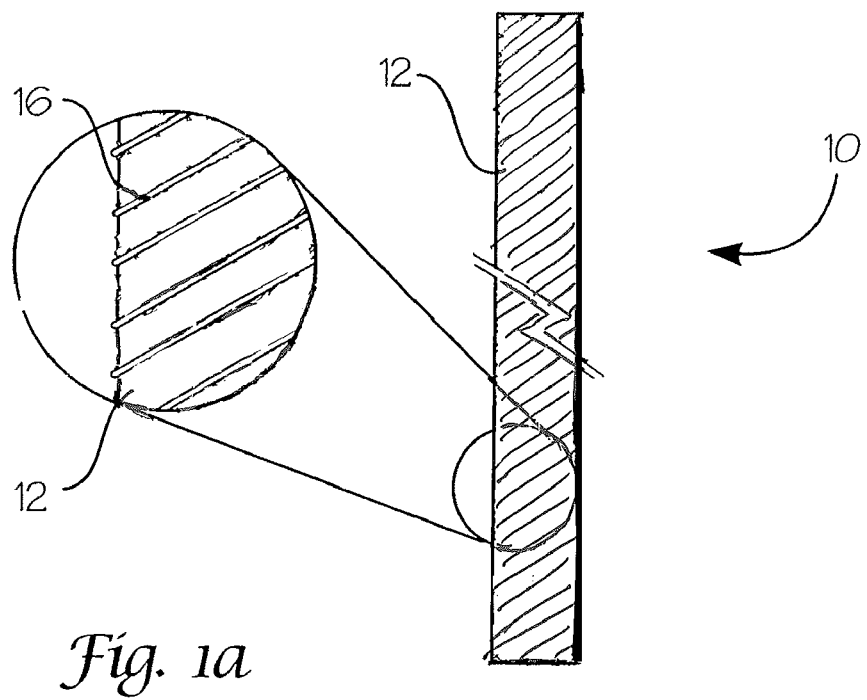
FIG. 1a is a side elevation view of an endoureteral stent in accordance with the present invention, in a planar configuration, with an exploded view of the fiber reinforcement.
Figure 1B:
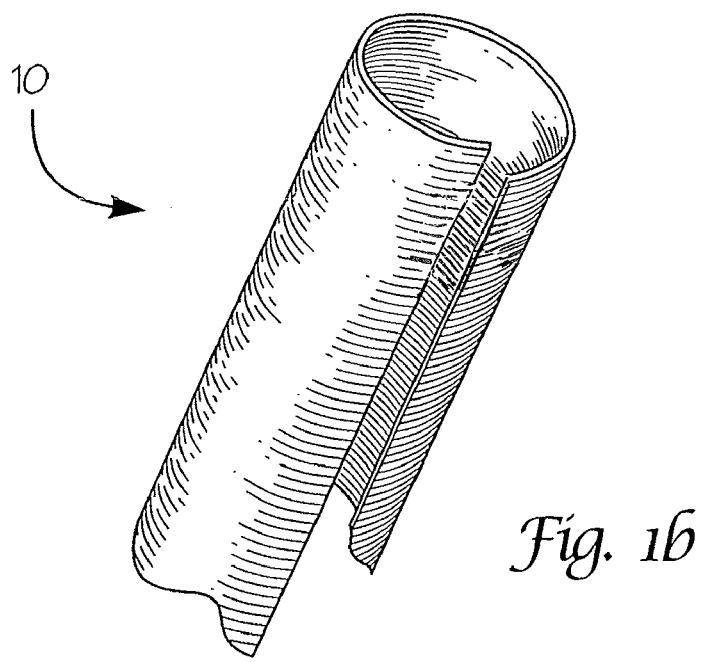
FIG. 1b is a perspective view of the stent of FIG. 1a in a curled configuration for use.

FIG. 1a illustrates an absorbable, multi-component, non-migrating endoureteral stent which is construct 10 of a fiber-reinforced elastomeric film 12. The break in the construct length represents the variable, customizable length of the stent. For the present embodiment the fiber-reinforcement is a monofilament coil 16. As shown in FIG. 1b, the fiber-reinforced elastomeric film is in the form of a slit tube that can be compressively overlapped under stress within a rigid, tubular applicator to yield a partially rolled configuration having an outside diameter that is at least two percent less than that of the patient ureter. When the stress is released at the site of a renal conduit upon discharging from the tubular applicator the slit edges spring back to acquire a nominal diameter that is at least on percent larger than that of biological conduit.

Figure 2:
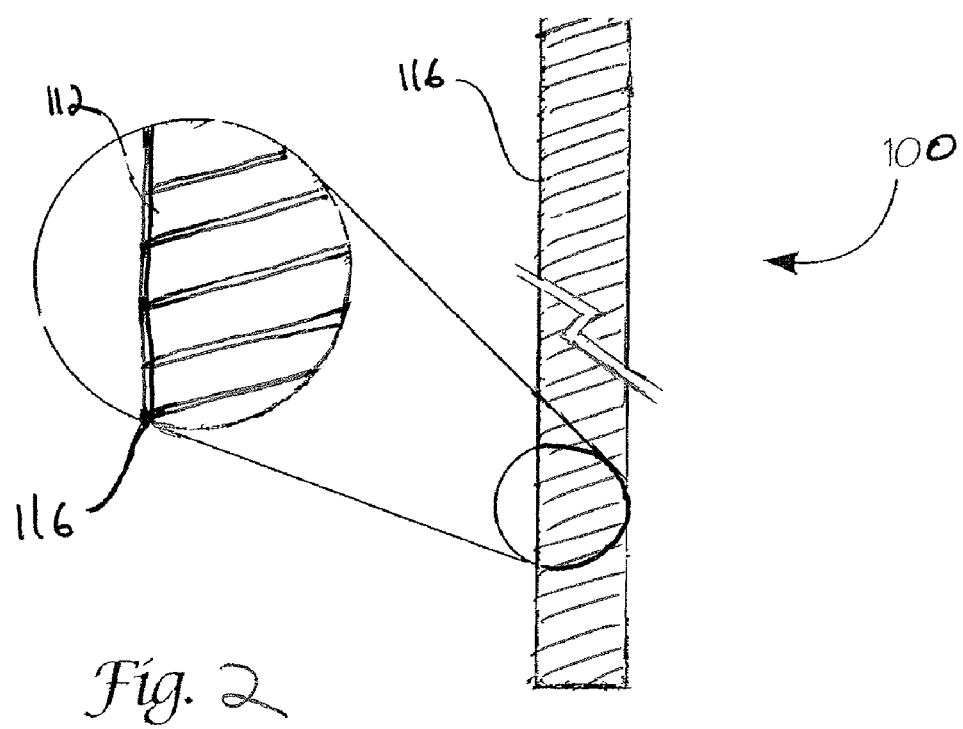
FIG. 2 is a side elevation view of an endoureteral stent in accordance with another embodiment of the present invention.

FIG. 2 illustrates another embodiment of the inventive endoureteral stent which includes a construct 100. The construct 100 includes a matrix 112 reinforced with a spring 116.

A significant aspect of this invention is the option to use solid polymeric microdispersion to produce the rigid filamentous scaffold or the compliant matrix. The solid dispersion is a unique concept which is based on using two partially miscible polyesters to form a melt blend where one of the polyesters will yield microdroplets which are dispersed in a continuous phase made of the second polyester. Achieving this condition requires certain interfacial tension in the melt, which can be modulated by allowing a certain amount of ester-ester interchange to lower the interfacial tension at will. This, in turn, can be modulated by controlling the processing temperature and time. During the production of the monofilament, the microdroplets elongate during extrusion to form microrods with an aspect ratio of more than 14 and a diameter of one to a few microns. As the monofilament solidifies, the elongated microdroplet (or microspindles) in the matrix form the perfect composite in terms of the filler-matrix adhesion. Further, orientation of the monofilament forces the microspindles (elongated microdroplets after solidification) to organize along the monofilament axis and cause a substantial increase in modulus and resilience. As the monofilament degrades, the matrix remains adhering to the spindles, which are overlapping through the entire matrix, until an advanced stage of degradation is reached. At this point, the matrix practically dissolves and the microspindles wash out as part of an aqueous/solid dispersion. An example of the multicomponent system suitable for this microcomposite may contain 90/10 and 15/85 glycolide/l-lactide as the continuous and dispersed phase, respectively. In one specific design, subject of this invention, during the production of the matrix component of the stent, the microdroplet of the multicomponent polyester converts to rigid microspheres that remain suspended in the compliant matrix so as to provide a high level of elasticity and flexibility. An example of the multicomponent system suitable for this microcomposite may contain 20/80 glycolide/ε-caprolactone segmented copolymer as a dispersed phase in a crosslinked, continuous phase made of 95/5 glycolide/caprolactone copolymer.

An important aspect of this invention deals with an absorbable/disintegratable endo-urological stent comprising a fiber-reinforced, multicomponent polymeric slit tube wherein the opposing edges of said slit can be compressively overlapped under stress within a rigid, tubular applicator to yield a partially rolled configuration having an outside diameter that is at least 2 percent less than that of the parent unslit tube and whenever the stress is released at the site of a renal conduit.

Upon discharging from the rigid tubular applicator the slit edges spring back almost instantly to acquire a nominal diameter that is at least 2 percent larger than that of the biological conduit wherein the reinforcing fibers of the multicomponent slit tube comprising a solid microdispersion made of (a) copolylactide dispersed phase having at least 65 percent of its chain repeat units derived from lactide and a copolyglycolide as the continuous phase having at least 65 percent of its chain repeat units derived from glycolide; (b) a copolycarprolactone dispersed phase having at least 90 percent of its chain repeat units derived from ε-caprolactone and a copolyglycolide as a continuous phase having at least 65 percent of its chain repeat units derived from glycolide; or (c) a copolycarprolactone dispersed phase having at least 90 percent of its chain repeat units derived from ε-caprolactone and copolylactide as a continuous phase having at least 65 percent of its chain repeat units derived from lactide.

A specific aspect of this invention deals with an absorbable/disintegratable endo-urological stent comprising a fiber-reinforced, multicomponent polymeric slit tube wherein the opposing edges of said slit can be compressively overlapped under stress within a rigid, tubular applicator to yield a partially rolled configuration having an outside diameter that is at least 2 percent less than that of the parent unslit tube and whenever the stress is released at the site of a renal conduit upon discharging from the rigid tubular applicator the slit edges spring back almost instantly to acquire a nominal diameter that is at least 2 percent larger than that of the biological conduit, wherein the reinforcing fibers of the multicomponent slit tube comprising a block copolymer of solid polyethylene glycol and a copolyester derived from one or more monomer selected from the group represented by l-lactide, glycolide, caprolactone, trimethylene carbonate and p-dioxanone. It is also preferred that such reinforcing fibers comprise highly oriented crystalline monofilaments having a tensile modulus that exceed 500 kpsi.

Another aspect of this invention deals with an absorbable/disintegratable endo-urological stent comprising a fiber-reinforced, multicomponent polymeric slit tube wherein the opposing edges of said slit can be compressively overlapped under stress within a rigid, tubular applicator to yield a partially rolled configuration having an outside diameter that is at least 2 percent less than that of the parent unslit tube and whenever the stress is released at the site of a renal conduit upon discharging from the rigid tubular applicator the slit edges spring back instantly to acquire a nominal diameter that is at least 2 percent larger than that of the biological conduit, wherein the slit fiber-reinforced multicomponent polymeric tube comprises a highly drawn monofilament as a reinforcing component to a crosslinked, compliant matrix. It is also preferred that the crosslinked matrix is based on a triaxial polyester with reactive itaconate end-groups and a chain derived from one or more monomer selected from the group represented by ε-caprolactone, trimethylene carbonate, glycolide, l-lactide, dl-lactide, and p-dioxanone.

Another aspect of this invention addresses a method for producing the absorbable/disintegratable slit-tube type endo-urological stent described above entailing the steps of (a) winding the highly drawn monofilament as described above onto a highly polished or Teflon-coated stainless steel rod with the desired outside diameter to yield the nominal diameter of the final device; (b) dip-coating the wound monofilament with the polyaxial polymer, with or without dilution with a solvent, of claim 8 that contains a moderate-temperature free-radical initiator, such as azo-bis-butyronitrile; (c) incremental heating of the assembled composite to achieve matrix curing; and (d) slitting the tube at one side longitudinally using laser or ultrasonic means.

A clinically relevant aspect of this invention deals with the slit-tube type endo-urological stent as described above and method for applying the stent as described above that entails the steps of (a) coating the external wall of the slit tube with an absorbable nonionic surfactant; (b) compress-folding, partially, the coated slit tube to yield a partially rolled configuration having a diameter that is at least 10 percent less than that of the original unslit tube; (c) inserting the partially rolled device into a relatively rigid tubular applicator made of polished stainless steel or high modulus polymer; (d) applying a nonionic absorbable surfactant on the outer surface of the applicator and inserting it into a hermetically sealable foil pack, under dry nitrogen, that comprises a dry cellulose applicator holder and a solid plunger (for discharging the device at the biological site); (e) sterilizing the slit tube in the applicator according to an accepted protocol; and (f) introducing the hollow component of the applicator using a plunger with a controlled motion arm that is barely touching the slit tube during insertion and able to push the slit tube out of the applicator following the disengagement of the motion arm from a special bay at the applicator wall.

Another major aspect of this invention deals with an absorbable/disintegratable endo-urological composite tubular stent comprising a highly elastomeric, water-swellable matrix reinforced with a rigid spring wherein (a) said spring comprising a multicomponent, high modulus, absorbable polymer; (b) the spring exhibiting a nominal diameter that is at least 2 percent less than that of the urological conduit sought for its application; (c) the elastomeric matrix component of the stent is made of a crosslinked absorbable copolymer that is asymmetrically placed to have more than 60 percent of its mass covering the outer surface of the spring; and (d) the elastomeric matrix component is capable of swelling in the biological environment to result in at least a 30 percent increase in thickness and a highly compliant surface intimately adhering to the lumen of the biological conduit, wherein the reinforcing fibers of the composite tubular stent comprising a solid microdispersion made of (a) a copolylactide dispersed phase having at least 65 percent of its chain repeat units derived from lactide and a copolyglycolide as the continuous phase having at least 65 percent of its chain repeat units derived from glycolide; (b) a copolycarprolactone dispersed phase having at least 90 percent of its chain repeat units derived from ε-caprolactone and a copolyglycolide as a continuous phase having at least 65 percent of its chain repeat units derived from glycolide; or (c) copolycarprolactone dispersed phase having at least 90 percent of its chain repeat units derived from ε-caprolactone and copolylactide as a continuous phase having at least 65 percent of its chain repeat units derived from lactide.

A specific aspect of this invention deals with an absorbable/disintegratable endo-urological composite tubular stent comprising a highly elastomeric, water-swellable matrix reinforced with a rigid spring wherein (a) said spring comprising a multicomponent, high modulus, absorbable polymer; (b) the spring exhibiting a nominal diameter that is at least 2 percent less than that of the urological conduit sought for its application; (c) the elastomeric matrix component of the stent is made of a crosslinked absorbable copolymer that is asymmetrically placed to provide more than 60 percent of its mass surrounding the outer surface of the spring; and (d) the elastomeric matrix component is capable of swelling in the biological environment to result in at least a 30 percent increase in thickness and a highly compliant surface intimately adhering to the lumen of the biological conduit, wherein the reinforcing spring of the multicomponent composite tube comprising a block copolymer of a solid polyethylene glycol and a copolyester derived from one or more monomer selected from the group represented by l-lactide, glycolide, caprolactone, trimethylene carbonate and p-dioxanone. It is also preferred that such reinforcing spring comprise highly oriented crystalline monofilaments having a tensile modulus that exceed 500 kpsi.

Another aspect of this invention deals with an absorbable/disintegratable endo-urological composite tubular stent comprising a highly elastomeric, water-swellable matrix reinforced with a rigid spring wherein (a) said spring comprising a multicomponent, high modulus, absorbable polymer; (b) the spring exhibiting a nominal diameter that is at least 2 percent less than that of the urological conduit sought for its application; (c) the elastomeric matrix component of the stent is made of a crosslinked absorbable copolymer that is asymmetrically placed to provide more than 60 percent of its mass surrounding the outer surface of the spring; and (d) the elastomeric matrix component is capable of swelling in the biological environment to result in at least a 30 percent increase in thickness and a highly compliant surface intimately adhering to the lumen of the biological conduit, wherein the spring reinforced multicomponent polymeric tube comprises a highly drawn monofilament as the reinforcing component to a crosslinked, compliant matrix. It is also preferred that the crosslinked matrix is based on a triaxial polyester with reactive itaconate end-groups and a chain derived from one or more monomer selected from the group represented by ε-caprolactone, trimethylene carbonate, glycolide, l-lactide, dl-lactide, and p-dioxanone.

Another aspect of this invention addresses a method for producing the absorbable/disintegratable endo-urological stent as described above entailing the steps of (a) winding the highly drawn monofilament onto a highly polished or Teflon-coated stainless steel rod with the desired outside diameter to yield the nominal internal diameter of the final device; (b) dip-coating the wound monofilament with the polyaxial polymer described earlier, with or without dilution with a solvent that contains a moderate-temperature free-radical initiator, such as azo-bis-butyronitrile; (c) adjust the coating thickness to provide required outside diameter of the device after curing/drying; and (d) incremental heating of the assembled composite to achieve matrix curing.

A clinically relevant aspect of this invention deals with the composite tubular-type endo-urological stent described above and method for assembling the construct for future use, which entails (a) coating the external wall with a nonionic, lubricous copolyester; (b) assembling in an applicator similar to those used for endovascular stent placement with an extensible balloon; and (c) sterilizing the assembled device in a hermetically sealed foil pack.

This invention also deals with a traditional method for introducing/inserting the endo-urological tubular stent which entails the use of a trocar.

Included in the preferred embodiments of the present invention is the incorporation in both types of stents described above of (1) bioactive agents including those having antimicrobial activities, and (2) radiopaque compounds, such as barium sulfate, zirconium oxide, or a ceramic material to allow radiographic monitoring of the placed stent. The radiopaque compound can be an inherent part of the stent or part of an adjoining marker.

Further illustrations of the present invention are provided by the following examples:

EXAMPLE 1

Preparation and Characterization of PEG-20k End-grafted with 90/10 l-Lactide/Caprolactone (P-I)

The PEG-20k (20 g) was dried at 110° C. under reduced pressure in a stirred reactor. To this, l-lactide (165.6 g) and ε-caprolactone (14.4 g) were added. The mixture was heated while stirring at 110° C. until a uniform solution is achieved. Stannous octanoate (207 mg) was then added to the polymerization mixture. After heating the latter to 160° C., the polymerization was continued for about 6 hours. The resulting polymer was isolated, ground, dried, and heated under reduced pressure at 110° C. to remove residual monomer. The polymer was characterized for identity and composition (IR and NMR), thermal properties (DSC), and molecular weight (GPC in dichloromethane). It was shown to have a $T_m=174°$ C. and molecular weight of about 94 kDa.

EXAMPLE 2

Preparation and Characterization of PEG 35k Endgrafted with l-Lactide/ε-Caprolactone (P-II)

Copolymer P-II was prepared under conditions similar to those used in the preparation of P-I in Example 1. The following amounts of intermediate and catalyst were used: PEG 35k, 30 g; l-lactide, 156.3 g; ε-caprolactone, 13.7 g; stannous octanoate, 244 mg. The resulting product was isolated, ground, purified, and characterized as described for P-I. The copolymer was shown to have a $T_m=175°$ C. and a molecular weight=75 kDa.

EXAMPLE 3

Preparation of Triaxial 90/10 (molar) ε-Caprolactone (CL)/Glycolide (G) Copolymer (P-III)

A mixture of CL (449.2 g) and glycolide (50.8 g) was mixed under dry nitrogen atmosphere in a predried reactor equipped for mechanical stirring. The polymerization was conducted under dry nitrogen atmosphere in the presence of trimethylol propane (8.38 g) as the initiator and stannous octanoate (2.73 mL of 0.2 M toluene solution) as the catalyst. The polymerization was completed after heating at 150° C. for 11 hours as determined by GPC. Traces of unreacted monomer were removed by distillation at 110° C. under reduced pressure. The molecular weight and thermal properties of the purified polymer were determined by GPC and DSC, respectively. The analytical data are summarized below: $M_n=17$ kDa; $M_w=25$ kDa; $T_m=44.7°$ C.; $\Delta H_f=58.3$ J/g

EXAMPLE 4

End-Capping of P-III with Itaconic Anhydride to Product P-III-IT

Copolymer P-III (220 g) from Example 3 was predried at 100° C. under reduced pressure for 30 minutes in a stirred reactor under nitrogen. The dried P-III was mixed with itaconic anhydride (64.4 g) and hydroquinone (111 mg). The reaction mixture was heated to 150° C. and maintained at that temperature while stirring for 4 hours. The capped product was isolated and characterized for identity and composition by NMR and IR. The product was stored under nitrogen at 4° C.

What is claimed is:

1. An absorbable endo-urological stent comprising a fiber-reinforced, multicomponent polymeric fully slit tube, wherein the slit extends along a longitudinal axis of the tube such that opposing edges of said slit can be compressively overlapped under stress within a rigid, tubular applicator to yield a partially rolled configuration having an outside diameter that is at least 2 percent less than that of the tube prior to slitting, such that when the stress is released at a site of a renal conduit upon discharging from the rigid tubular applicator the opposing edges spring back to acquire a diameter that is at least 2 percent larger than that of the renal conduit, the fiber-reinforcement comprising a coiled reinforcing fiber that is an extruded monofilament of a solid microdispersion made of one of the following:
   (a) a copoly-lactide dispersed phase in a copolyglycolide continuous phase,
   (b) a copoly-caprolactone dispersed phase in a copolyglycolide continuous phase, or
   (c) a copoly-caprolactone dispersed phase in a copoly-lactide continuous phase;
   wherein the dispersed phase is in the form of microspindles organized and overlapping along the monofilament axis thereby increasing the tensile modulus and resilience of the monofilament.

2. An absorbable endo-urological stent as in claim 1 wherein the solid microdispersion comprises a copoly-lactide dispersed phase having at least 65 percent of its chain repeat units derived from lactide and a copolyglycolide as the continuous phase having at least 65 percent of its chain repeat units derived from glycolide.

3. An absorbable endo-urological stent as in claim 1 wherein the solid microdispersion comprises a copoly-caprolactone dispersed phase having at least 90 percent of its chain repeat units derived from ε-caprolactone and a copolyglycolide as a continuous phase having at least 65 percent of its chain repeat units derived from glycolide.

4. An absorbable endo-urological stent as in claim 1 wherein the solid microdispersion comprises a copolycarprolactane dispersed phase having at least 90 percent of its chain repeat units derived from ε-caprolactone and copolylactide as a continuous phase having at least 65 percent of its chain repeat units derived from lactide.

5. An absorbable endo-urological stent as in claim 1 wherein said extruded monofilament reinforces a crosslinked, compliant matrix.

6. An absorbable endo-urological stent as in claim 5 wherein the crosslinked matrix is based on a triaxial polyester with reactive itaconate end-groups and a chain derived from at least one monomer selected from the group consisting of ε-caprolactone, trimethylene carbonate, glycolide, l-lactide, dl-lactide, and p-dioxanone.

7. An absorbable endo-urological stent as set forth in claim 1 containing at least one antimicrobial agent.

8. An absorbable endo-urological stent as set forth in claim 1 containing a radipaque compound.

9. An absorbable endo-urological composite tubular stent comprising an elastomeric, water-swellable matrix reinforced with a rigid spring wherein (a) said spring comprises a multicomponent and absorbable polymer; (b) the spring exhibits a nominal diameter that is at least 2 percent less than that of the urological conduit sought for its application; (c) the matrix is made of a crosslinked absorbable copolymer that is asymmetrically placed to have more than 60 percent of its mass covering the outer surface of the spring; and (d) the matrix is capable of swelling in a biological environment to result in at least a 30 percent increase in thickness and a compliant surface intimately adhering to a lumen of the urological conduit, wherein the spring is an extruded monofilament of a solid microdispersion made of one of the following:
   (a) a copoly-lactide dispersed phase in a copolyglycolide continuous phase,
   (b) a copoly-caprolactone dispersed phase in a copolyglycolide continuous phase, or
   (c) a copoly-caprolactone dispersed phase in a copoly-lactide continuous phase;
   wherein the dispersed phase is in the form of microspindles organized and overlapping along the monofilament axis thereby increasing the tensile modulus and resilience of the monofilament.

10. An absorbable endo-urological stent as in claim 9 wherein the solid microdispersion comprises a copolytactide dispersed phase having at least 65 percent of its chain repeat units derived from lactide and a copolyglycolide as the continuous phase having at least 65 percent of its chain repeat units derived from glycolide.

11. An absorbable endo-urological stent as in claim 9 wherein the solid microdispersion comprises a copoly-caprolactone dispersed phase having at least 90 percent of its chain repeat units derived from ε-caprolactone and a copolyglycolide as a continuous phase having at least 65 percent of its chain repeat units derived from glycolide.

12. An absorbable endo-urological stent as in claim 9 wherein said solid microdispersion comprises a copoly-carprolactone dispersed phase having at least 90 percent of its chain repeat units derived from ε-caprolactone and a copolyglycolide as a continuous phase having at least 65 percent of its chain repeat units derived from lactide.

13. An absorbable endo-urological stent as in claim 9 wherein the extruded monofilament reinforces the matrix.

14. An absorbable endo-urological stent as in claim 13 wherein the crosslinked absorbable copolymer of the matrix is based on a triaxial polyester with reactive itaconate end-groups and a chain derived from at least one monomer selected from the group consisting of ε-caprolactone, trimethylene carbonate, glycolide, l-lactide, dl-lactide, and p-dioxanone.

15. An absorbable endo-urological composite tubular stent as in claim 9 containing one or more antimicrobial agent.

16. An absorbable endo-urological composite tubular stent as in claim 9 containing a radiopaque compound.

* * * * *